United States Patent
Goto et al.

(10) Patent No.: US 9,714,410 B2
(45) Date of Patent: Jul. 25, 2017

(54) CELL CULTURE METHOD AND UTILIZATION OF THE SAME

(75) Inventors: Susumu Goto, Tokyo (JP); Shohei Kishishita, Tokyo (JP); Shinya Takuma, Tokyo (JP); Chikashi Hirashima, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 9 days.

(21) Appl. No.: 11/793,784

(22) PCT Filed: Dec. 26, 2005

(86) PCT No.: PCT/JP2005/023709
§ 371 (c)(1),
(2), (4) Date: Jun. 21, 2007

(87) PCT Pub. No.: WO2006/073070
PCT Pub. Date: Jul. 13, 2006

(65) Prior Publication Data
US 2008/0124761 A1    May 29, 2008

(30) Foreign Application Priority Data
Jan. 5, 2005  (JP) ................. 2005-000747

(51) Int. Cl.
*C12N 5/00* (2006.01)
*C12N 5/18* (2006.01)

(52) U.S. Cl.
CPC ........ *C12N 5/0037* (2013.01); *C12N 2500/80* (2013.01); *C12N 2510/02* (2013.01)

(58) Field of Classification Search
USPC ....... 435/358, 384, 404, 69.1, 41, 440, 70.1, 435/391; 530/387.1
See application file for complete search history.

(56) References Cited

U.S. PATENT DOCUMENTS

| | | | |
|---|---|---|---|
| 5,401,653 A | 3/1995 | Sawyer et al. | |
| 5,426,045 A | 6/1995 | Sawyer et al. | |
| 5,443,894 A | 8/1995 | Pollock et al. | |
| 5,498,540 A | 3/1996 | Sawyer et al. | |
| 6,537,782 B1 | 3/2003 | Shibuya et al. | |
| 7,709,615 B2 * | 5/2010 | Irie ................ | C07K 16/00 536/23.1 |
| 7,993,642 B2 * | 8/2011 | Tsunoda ........... | C07K 16/28 424/141.1 |
| 2003/0096372 A1 | 5/2003 | Shibuya et al. | |

FOREIGN PATENT DOCUMENTS

| | | |
|---|---|---|
| EP | 1 085 083 A1 | 3/2001 |
| EP | 1 342 780 A1 | 9/2003 |
| EP | 1 652 925 A1 | 5/2006 |
| JP | 04-501660 A | 3/1992 |
| JP | 2003-250533 A | 9/2003 |
| JP | 2003-334068 A | 11/2003 |
| WO | WO 90/03430 A1 | 4/1990 |
| WO | WO 95/23212 A1 | 8/1995 |
| WO | WO 99/63058 A1 | 12/1999 |
| WO | WO 2004/099396 A1 | 11/2004 |
| WO | WO 2005/005636 * | 1/2005 |
| WO | WO 2005/005636 A1 | 1/2005 |
| WO | WO 2005/056604 * | 6/2005 |

OTHER PUBLICATIONS

Xie et al., Biotechnology and Bioengineering 56(5):577-582, 1997.*
Omasa et al. Cytotechnology 8(1):75-84, 1992.*
Wurm, F., Nature Biotechnology 22(11):1393-1398, published online Nov. 4, 2004.*
Frahm et al., "Improvement of a mammalian cell culture process by adaptive, model-based dialysis fed-batch cultivation and suppression of apoptis," Bioprocess Biosyst. Eng., 2003, 26:1-10.
Supplementary European Search Report dated Sep. 9, 2009, in corresponding EP 05819639.5, 7 pages.
Page et al., "Growth of *Azotobacter vinelandii* UWD in Fish Peptone Medium and Simplified Extraction of Poly-β-Hydroxybutyrate," Applied and Environmental Microbiology, Dec. 1993, 59(12):4236-4244.
Sun et al., "Growth and metabolism of Chinese hamster ovary cells cultured in bioreactor," Journal of Yunnan University, 2002, 24(5):388-392, with English Abstract on last page.
Gu et al., "Influence of Primatone RL Supplementation on Sialylation of Recombinant Human Interferon-γ Produced by Chinese Hamster Ovary Cell Culture Using Serum-Free Media," Biotechnology and Bioengineering, Nov. 20, 1997, 56(4):353-360.
Zeng et al,. "Mathematical Modeling and Analysis of Glucose and Glutamine Utilization and Regulation in Cultures of Continuous Mammalian Cells," Biotechnology and Bioengineering, Aug. 5, 1995, 47(3):334-346.
Xie et al., "High Cell Density and High Monoclonal Antibody Production Through Medium Design and Rational Control in a Bioreactor," Biotechnology and Bioengineering, 1996, 51:725-729.

* cited by examiner

*Primary Examiner* — Delia Ramirez
(74) *Attorney, Agent, or Firm* — Foley & Lardner LLP

(57) ABSTRACT

It is an object of the present invention to allow a cell to produce a protein at a high level using a medium containing an enzymatic degradation product of fish meat or a fish meat extract. A method of culturing a cell comprising starting culturing in an initial medium and feeding at least once a feed medium to the initial medium during culturing, wherein at least one of the initial medium or the feed medium contains an enzymatic degradation product of fish meat or a fish meat extract added thereto. A method of producing a protein of interest using the above culture method.

5 Claims, 2 Drawing Sheets

CELL CULTURE METHOD AND UTILIZATION OF THE SAME

CROSS REFERENCE TO RELATED APPLICATIONS

This application is a National Stage application of PCT/JP2005/023709, filed Dec. 26, 2005, which claims priority from Japanese patent application JP 2005-000747, filed Jan. 5, 2005.

TECHNICAL FIELD

The present invention relates to a method of culturing a cell and use of the method. More specifically, the present invention relates to a method of culturing a cell and a method of allowing a cell to produce a protein utilizing the above method.

BACKGROUND ART

In culturing an animal cell to obtain a natural protein produced by the animal cell, or in culturing an animal cell incorporating a gene encoding a desired protein to produce the desired protein, etc., essential nutrients, such as bases, sugars, amino acids, and vitamins, are added to a culture medium. Further, a mammal-derived extract, concretely, serum such as fetal bovine serum, is usually added in a range of 5 to 20% for proliferation of the animal cell. However, such mammal-derived serum has a number of drawbacks. It accounts for 75 to 95% of the cost for the culture medium, and because of inter-lot differences existing in quality, stable proliferation is not achieved. Moreover, the mammal-derived serum cannot be sterilized in an autoclave or the like, and thus may be contaminated with viruses or mycoplasmas. Although most of these viruses or mycoplasmas are non-pathogenic, they can become additional unknown factors from the viewpoint of stable manufacture. Furthermore, the serum contains more than 500 types of proteins, thus complicating the isolation and purification of the desired protein, the cell product, from the cultured medium. To resolve such problems with stable manufacture, methods using a serum-derived purified protein such as fetuin, insulin or transferrin, instead of serum, are performed. Methods, which use culture medium components extracted from mammals, are also attempted from the viewpoint of production cost.

Recently, however, concern has been expressed over the relation between mammal-derived components and diseases such as mad cow disease, bovine spongiform encephalopathy (BSE), transmissible spongiform encephalopathy (TSE), and Creutzfeld-Jakob disease (CJD). The development of a culture medium for culturing animal cells free from these mammal-derived components has been demanded from the viewpoint of safety.

In culturing an animal cell, the failure to add the above-described mammal-derived components into the culture medium causes a marked drop in the survival rate of cells, and a decrease in viable cell count in the culture broth, at an early stage of culture. These events make long-term culture or large-scale culture impossible.

In order to solve the above-described problem, a method in which an enzymatic degradation product of fish meat or a fish meat extract is added to the culture medium has been reported (Patent Documents 1 and 2). With this method, high production of protein has become possible without fetal bovine serum which was generally believed essential.

However, further improvement has been desired because still higher levels of protein production are preferable from the viewpoint of production cost.

Patent Document 1: International Publication WO 99/63058
Patent Document 2: Japanese Unexamined Patent Publication No. 2003-334068

DISCLOSURE OF THE INVENTION

Problem for Solution by the Invention

It is an object of the present invention to allow a cell high production of protein by performing fed-batch culture using a medium containing an enzymatic degradation product of fish meat or a fish meat extract.

Means to Solve the Problem

As a result of extensive and intensive researches toward solution of the above-described problem, the prevent inventors have found that is it possible to allow a cell to produce a protein of interest at a still higher yield by performing fed-batch culture using a medium containing an enzymatic degradation product of fish meat or a fish meat extract added thereto. Thus, the present invention has been achieved.

The subject matters of the present invention are as described below.

(1) A method of culturing a cell comprising starting culturing in an initial medium and feeding at least once a feed medium to the initial medium during culturing, wherein at least one of the initial medium or the feed medium contains an enzymatic degradation product of fish meat or a fish meat extract added thereto.

(2) A method of culturing a cell comprising starting culturing in a medium containing an enzymatic degradation product of fish meat or a fish meat extract added thereto and feeding at least once an enzymatic degradation product of fish meat or a fish meat extract to the medium during culturing.

(3) The method of (2), wherein the cell is cultured by fed-batch culture.

(4) The method of any one of (1) to (3), wherein the cell is a cell into which a gene encoding a protein of interest has been transferred.

(5) The method of (4), wherein the protein of interest is an antibody.

(6) The method of any one of (1) to (5), wherein the cell is an animal cell.

(7) The method of (6), wherein the cell is a mammal cell.

(8) The method of (7), wherein the mammal cell is a CHO cell.

(9) A method of producing a protein by culturing a cell, comprising starting culturing in an initial medium and feeding at least once a feed medium to the initial medium during culturing, wherein at least one of the initial medium or the feed medium contains an enzymatic degradation product of fish meat or a fish meat extract added thereto.

(10) A method of producing a protein by culturing a cell, comprising starting culturing in a medium containing an enzymatic degradation product of fish meat or a fish meat extract added thereto and feeding at least once an enzymatic degradation product of fish meat or a fish meat extract to the medium during culturing.

(11) The method of (10), wherein the cell is cultured by fed-batch culture.

(12) The method of any one of (9) to (11), wherein the cell is a cell into which a gene encoding a protein of interest has been transferred.
(13) The method of (12), wherein the protein of interest is an antibody.
(14) The method of any one of (9) to (13), wherein the cell is an animal cell.
(15) The method of (14), wherein the cell is a mammal cell.
(16) The method of (15), wherein the mammal cell is a CHO cell.

Effect of the Invention

In the present invention, it is possible to allow a cell to produce a protein of interest at a still higher yield by adding an enzymatic degradation product of fish meat or a fish meat extract not only to the medium at the start of culturing but also to the medium during culturing.

The present specification encompasses the contents described in the specification and/or the drawings of Japanese Patent Application No. 2005-000747 based on which the present patent application claims priority.

BEST MODE FOR CARRYING OUT THE INVENTION

Figure 1:
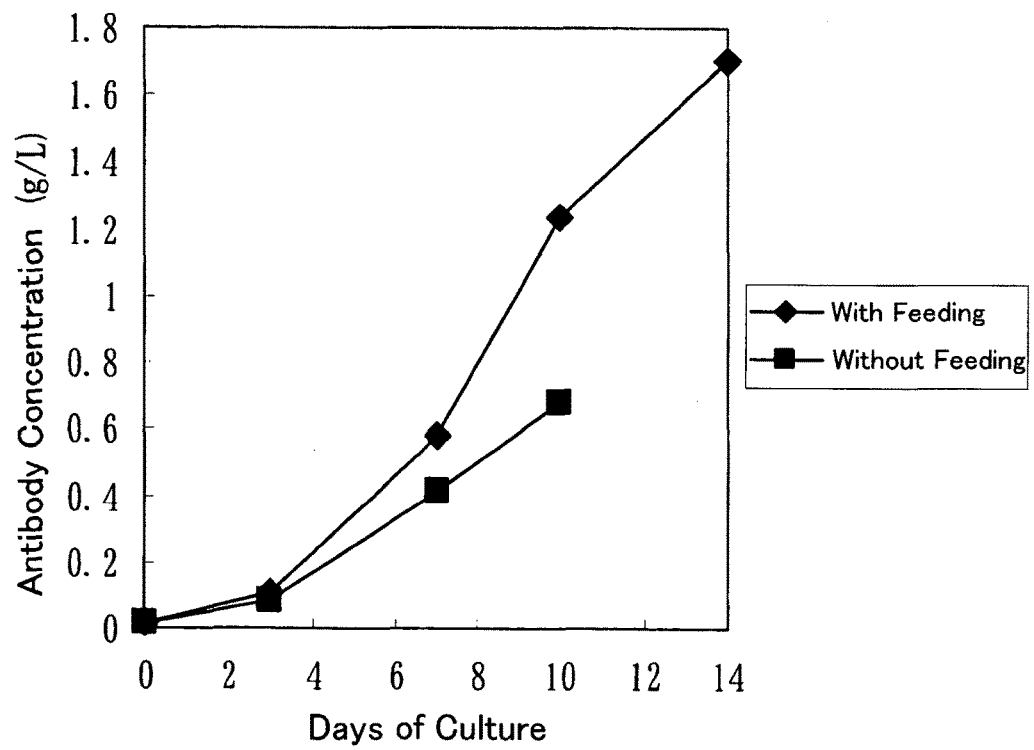
FIG. 1 is a graph showing the concentrations (g/L) of an antibody produced in culture media by CHO cells which were cultured in a mammal-derived component free medium supplemented with 5 g/L of bonito hydrolysate (initial medium) and a mammal-derived component free medium supplemented with 30 g/L of bonito hydrolysate (feed medium).

Hereinbelow, the present invention will be described in more detail.

In the present invention, culturing a cell is started in an initial medium, to which a feed medium is fed at least once during culturing. At least one of the initial medium or the feed medium contains an enzymatic degradation product of fish meat or a fish meat extract added thereto.

Further, in a preferred embodiment of the present invention, culturing a cell is started in a medium containing an enzymatic degradation product of fish meat or a fish meat extract, and at least once an enzymatic degradation product of fish meat or a fish meat extract is fed to the medium during culturing.

According to the present invention, it is possible to culture a cell satisfactorily in a medium generally used as a conventional, animal cell culture medium without adding mammal-derived components.

Generally, cell culture methods are classified into batch culture, continuous culture and fed-batch culture. In the present invention, any of these methods may be used. Preferably, fed-batch culture or continuous culture is used. More preferably, fed-batch culture is used.

Batch culture is a culture method in which a small amount of seed culture is added to a medium and the cell is grown therein without feeding of fresh medium or removal of culture broth during culturing.

Continuous culture is a culture method in which a medium is continuously fed and continuously removed during culturing. Perfusion culture is also included in continuous culture.

Since fed-batch culture is intermediate between batch culture and continuous culture, it is also called semi-batch culture. During culturing, medium is fed continuously or intermittently, but continuous removal of culture broth as seen in continuous culture is not performed. The medium which is fed in fed-batch culture (hereinafter, called "feed medium") may not be the same medium as already used in the relevant culturing (hereinafter called "initial medium"). A different medium may be fed or a specific component alone may be fed.

In the present invention, the term "initial medium" means a medium which is usually used at the first stage of cell culture. However, when a feed medium is fed in portions a plurality of times, the medium before the feeding of each portion of the feed medium may be regarded as an initial medium.

In the method of the present invention, when fed-batch culture is employed, an enzymatic degradation product of fish meat or a fish meat extract may be contained in either one of the feed medium or the initial medium. Preferably, an enzymatic degradation product of fish meat or a fish meat extract is contained in both the feed medium and the initial medium. Furthermore, it is preferred that the concentration of fish meat enzymatic degradation product or fish meat extract in the feed medium be higher than the corresponding concentration in the initial medium. The concentration of fish meat enzymatic degradation product or fish meat extract in the initial medium may be usually 1-30 g/L, preferably 3-20 g/L, more preferably 5-15 g/L. The concentration of fish meat enzymatic degradation product or fish meat extract in the feed medium may be usually 5-150 g/L, preferably 10-120 g/L, more preferably 20-90 g/L, still more preferably 30-75 g/L. The volume ratio between the initial medium and the feed medium is not particularly limited. Usually, when the volume of the initial medium is taken as 1, the ratio of the feed medium is 0.01-10, preferably 0.1-1, more preferably 0.2-0.3. The feed medium may be fed continuously or from time to time. When fed from time to time, the number of times of feeding is not particularly limited. The feed medium may be fed once or plurality of times.

With respect to the enzymatic degradation product of fish meat or fish meat extract used in the present invention, examples of fish meat include the fish meat of red fleshed fishes, such as bonito, frigate mackerel, tuna, mackerel, pacific saury, sardine, horse mackerel, and salmon; and the fish meat of white fleshed fishes, such as cod, Japanese sea bass, right-eyed flounder, left-eyed flounder, and sea bream. The preferred examples are bonito, frigate mackerel, cod, mackerel, salmon, and sardine.

The fish meat extract used in the present invention can be obtained by cutting the fish meat into suitable pieces, or mincing the fish meat into a pasty form, and extracting soluble components of the pieces or the paste with hot water (for example, hot water at 90 to 95° C.) for several tens of minutes to several tens of hours. Specific examples include stock made from boiled bonito for production of dried bonito, and cook drain during production of canned foods.

The enzyme degradation product of fish meat can be obtained, for example, by adding a suitable amount of water to cooked fish meat as it is, or fish meat minced to a paste, or the above fish meat extract, followed, if necessary, by heating for protein denaturation, then treating the material with a protease, and centrifuging or filtering the treated material as desired, to remove oils and insolubles. The resulting fish meat extract or the enzymatic degradation product of fish meat is desirably adjusted to pH 7 to 7.4 before use.

The protease used in the present invention is, for example, a proteinase and/or a peptidase. As used herein, the term "proteinase" refers to an enzyme which hydrolyzes a protein as a substrate, while the term "peptidase" refers to a peptide bond hydrolase for a peptide as a substrate. That is, the activity of the protease against the protein substrate can be distinguished as proteinase activity, while the activity of the protease against the peptide substrate can be distinguished as peptidase activity. When catalyzing cleavage of a peptide bond chain, at its intermediate site, by the activity of protease against the protein substrate, the term "proteinase" is used. Hence, endopeptidase is used herein as one of proteinases.

Specific examples of enzymes to be used in the present invention include enzymes of plant origin, such as papain, chymopapain, bromelain, and ficin, and enzymes from microorganisms, such as molds, bacteria, and yeast. They include endopeptidase, exopeptidase, aminopeptidase, carboxypeptidase, and dipeptidase. These enzymes can be used alone or in combination. When they are combined, they may be added at the same time, or progressively.

The enzymatic degradation product of fish meat in the present invention is preferably an enzymatic degradation product of fish meat obtained by treatment with the proteinase, followed by treatment with the peptidase.

The conditions for treatment with enzymes differ depending on the type of the enzyme used. Usually, the enzyme treatment is performed at pH 2 to 12, preferably pH 4 to 8, at 30 to 90° C., preferably 40 to 65° C., for 30 minutes to 72 hours, preferably 3 to 24 hours. The enzyme is used at about 0.001 to 10 w/w %, preferably 0.1 to 1 w/w %, more preferably 0.2-0.6 w/w %, relative to the protein as the substrate. The enzyme in the resulting enzymatic degradation product of fish meat is inactivated by heating or the like, and performing centrifugation or filtration as desired, to remove oils and insolubles, whereby the enzymatic degradation product can be prepared.

Fish meat comprises fish guts and proper meat. The ratio between guts and proper meat is not particularly limited and any ratio may be used. For example, the ratio disclosed in Japanese Unexamined Patent Publication No. 2003-334068 may be used.

With respect to other components of the culture medium used in the present invention, various components usually used in cell (preferably animal cell) culture media can be used appropriately. They include amino acids, vitamins, lipid factors, energy sources, osmotic regulators, iron sources and pH regulators. In addition to these components, trace metal elements, surfactants, growth cofactors, nucleosides, and the like may be added.

Specific examples of such components include amino acids, such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine, preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, and L-valine; vitamins, such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin B.sub.12, and ascorbic acid, preferably, biotin, folic acid, lipoic acid, nicotinamide, calcium pantothenate, pyridoxal hydrochloride, riboflavin, thiamine hydrochloride, vitamin B.sub.12, and ascorbic acid; lipid factors, such as choline chloride, choline tartrate, linoleic acid, oleic acid, and cholesterol, preferably, choline chloride; energy sources, such as glucose, galactose, mannose, and fructose, preferably, glucose; osmotic regulators, such as sodium chloride, potassium chloride, and potassium nitrate, preferably, sodium chloride; iron sources, such as iron EDTA, ferric citrate, ferrous chloride, ferric chloride, ferrous sulfate, ferric sulfate, and ferric nitrate, preferably, ferric chloride, iron EDTA, and ferric citrate; and pH regulators, such as sodium bicarbonate, calcium chloride, sodium phosphate monobasic, HEPES, and MOPS, preferably, sodium bicarbonate. Culture media containing any of these components can be given as examples.

Besides the above components, there may be added trace metal elements, such as copper sulfate, manganese sulfate, zinc sulfate, magnesium sulfate, nickel chloride, tin chloride, magnesium chloride, and sodium subsilicate, preferably, copper sulfate, zinc sulfate, and magnesium sulfate; surfactants, such as Tween 80, and Pluronic F68; growth cofactors, such as recombinant insulin, recombinant IGF, recombinant EGF, recombinant FGF, recombinant PDGF, recombinant TGF-α, ethanolamine hydrochloride, sodium selenite, retinoic acid, and putrescine dihydrochloride, preferably, sodium selenite, ethanolamine hydrochloride, recombinant IGF, and putrescine dihydrochloride; and nucleosides, such as deoxyadenosine, deoxycytidine, deoxyguanosine, adenosine, cytidine, guanosine, and uridine. In the preferred embodiments of the present invention described above, antibiotics, such as streptomycin, penicillin-G potassium, and gentamicin, and pH-indicators, such as Phenol Red, may be contained.

The medium used in the present invention may be prepared by adding an enzymatic degradation product of fish meat or a fish meat extract to a commercial, animal cell culture medium, such as D-MEM (Dulbecco's Modified Eagle Medium), D-MEM/F-12 1:1 Mixture (Dulbecco's Modified Eagle Medium: Nutrient Mixture F-12), RPMI1640, CHO-S-SFMII (Invitrogen), CHO-SF (Sigma-Aldrich), EX-CELL 301 (JRH Biosciences), CD-CHO (Invitrogen), IS CHO-V (Irvine Scientific) or PF-ACF-CHO (Sigma-Aldrich).

In the present invention, the medium to which an enzymatic degradation product of fish meat or a fish meat extract is added is not particularly limited, and any medium may be used. Preferably, a serum free medium which does not contain any mammal-derived serum may be used. In particular, a mammal-derived component free medium which does not contain any mammal-derived component isolated from mammals is preferred.

When the medium to which an enzymatic degradation product of fish meat or a fish meat extract is added is a serum free medium or an animal-derived component free medium, usually, the cell to be cultured is adapted in advance to that the cell can grow in such a medium. The method of conditioning cells is well-known to those skilled in the art.

The amounts of the other components in the culture medium are 0.05 to 1,500 mg/L for amino acids, 0.001 to 10 mg/L for vitamins, 0 to 200 mg/L for lipid factors, 1 to 20 g/L for energy sources, 0.1 to 10,000 mg/L for osmotic regulators, 0.1 to 500 mg/L for iron sources, 1 to 10,000 mg/L for pH buffers, 0.00001 to 200 mg/L for trace metal elements, 0 to 5,000 mg/L for surfactants, 0.05 to 10,000 µg/L for growth cofactors, and 0.001 to 50 mg/L for nucleosides. These amounts can be determined appropriately depending on the type of the cell to be cultured, and the type of the protein of interest.

The pH of the culture medium differs depending on the cell to be cultured, but is generally pH 6.8 to 7.6 and appropriately pH 7.0 to 7.4 in many cases.

The culture method of the invention may be used, without any restriction, for culturing various cells (e.g., bacterial cells, fungal cells, insect cells, plant cells, animal cells, etc.). For example, a COS cell or CHO cell having a gene encoding a protein of interest incorporated by genetic engineering procedures, or an antibody-producing fusion cell represented by a hybridoma, such as mouse-human, mouse-mouse, or mouse-rat may be cultured by the method of the present invention. The culture method of the present invention may also be used when an animal cell is cultured to obtain a natural protein produced by the animal cell. The culture method may also be used for culturing BHK cells and HeLa cells as well as the above-mentioned cells.

A particularly preferable animal cell in the present invention is a CHO cell into which a gene encoding a protein of interest has been transferred. The protein of interest is not particularly limited and may be any protein such as an antibody (natural antibody, low molecular sized antibody, chimeric antibody, humanized antibody, etc.) or a physiologically active protein (granulocyte colony-stimulating factor (G-CSF), granulocyte-macrophage colony-stimulating factor (GM-CSF), erythropoietin, interferon, interleukin such as IL-1 or IL-6, t-PA, urokinase, serum albumin, blood coagulation factor, etc.). Among all, an antibody is especially preferred.

Examples of antibodies produced by the production method of the present invention include not only monoclonal antibodies derived from animals such as human, mouse, rat, hamster, rabbit, monkey or the like but also artificially modified recombinant antibodies such as chimeric antibodies, humanized antibodies, bispecific antibodies or the like. The immunoglobulin class of these antibodies is not particularly limited, and may be any class such as IgG (IgG1, IgG2, IgG3, IgG4, etc.), IgA, IgD, IgE, IgM or the like. When the antibody is to be used as a pharmaceutical, the class is preferably IgG or IgM. Furthermore, the antibody of the present invention encompasses not only whole antibodies but also antibody fragments (such as Fv, Fab, F(ab)$_2$) and low molecular sized antibodies, e.g., single chain Fv (scFV, sc(FV)$_2$, etc.) of monovalence or divalence or higher valence prepared by linking variable regions of antibodies with a linker such as peptide linker.

The culture conditions differ depending on the type of the cell used, and preferable conditions may be determined as desired. For example, when the cell is a CHO cell, it may be cultured usually in an atmosphere with a $CO_2$ concentration in a gas phase of 0 to 40%, preferably 2 to 10%, at 30 to 39° C., preferably about 37° C., for 1 to 14 days.

Culture can be performed using various culture devices for animal cell culture, for example, a fermentor type tank culture device, an air lift type culture device, a culture flask type culture device, a spinner flask type culture device, a microcarrier type culture device, a fluidized bed type culture device, a hollow fiber type culture device, a roller bottle type culture device, and a packed bed type culture device.

High production of protein becomes possible by culturing a cell (preferably, animal cell) according to the method of the present invention.

To produce a protein in an animal cell, mere culture may suffice, or a special procedure may be required. The procedures, conditions, etc. may be determined, as required, depending on the animal cell to be cultured. In the case of a CHO cell transformed with a vector containing a gene encoding a mouse-human chimeric antibody by a genetic engineering operation, for example, culture is performed under the aforementioned conditions, whereby the protein of interest can be obtained in the culture medium in about 1 to 14 days, preferably in about 7 to 10 days. Then, the culture medium is subjected to isolation and purification by conventional methods (see, for example, Introduction to Antibody Engineering, Chijin Sho Kan publishing company, pp. 102-104; Affinity Chromatography Principles & Methods, Amersham Pharmacia Biotech, pp. 56-60), whereby the protein of interest can be obtained.

According to the present invention, it is possible to produce a recombinant antibody (natural antibody, antibody fragment, low molecular sized antibody, chimeric antibody, humanized antibody, bispecific antibody, etc.), a recombinant protein (granulocyte colony-stimulating factor (G-CSF), granulocyte-macrophage colony-stimulating factor (GM-CSF), erythropoietin, interferon, interleukin such as IL-1 or IL-6, t-PA, urokinase, serum albumin, blood coagulation factor, etc.) or the like at a high yield.

EXAMPLES

Hereinbelow, the present invention will be described in more detail with reference to the following Examples and Reference Example. These examples are intended to illustrate the present invention and not to limit the scope of the present invention.

Example 1

Fed-Batch Culture Using a Bonito Hydrolysate

The compositions of the media and the method of preparation thereof are as described below.

Initial Medium: The bonito hydrolysate prepared in Reference Example 1 was added to a mammal-derived component free medium at 5 g/L. After dissolution, the resultant medium was filter-sterilized.

Feed Medium: The concentrations of the components in the mammal-derived component free medium used as the initial medium were made about 2-fold relative to the initial medium. The bonito hydrolysate (30 g/L) was added to the resultant medium and dissolved, followed by filter sterilization.

Cell: Recombinant anti-ganglioside GM3 human antibody (L612)-producing CHO cell strain disclosed in International Publication WO 2005/005636. The class of this antibody is IgM.

The initial medium was added to a jar-type culture device. The above-described CHO cell strain was added thereto at $2 \times 10^5$ cells/mL. Then, culturing was started at 37° C. under 10% $CO_2$. In fed-batch culture, the feed medium was fed at a constant flow rate from day 3 of culture, and cells were cultured until day 14. Sampling was performed at the start of culture and at days 3, 7, 10 and 14. The culture supernatant of each sample was subjected to size exclusion chromatography to determine the concentration of antibody produced. As shown in FIG. 1, the antibody concentration was about 0.6 g/L after 10 days culture when the feed medium was not fed. On the other hand, when the solution containing the bonito hydrolysate was fed, high antibody concentrations could be achieved (1.2 g/L or more after 10 days culture and exceeding 1.7 g/L after 14 days culture).

Example 2

Fed-Batch Culture Using a Bonito Hydrolysate

The compositions of the media and the method of preparation thereof are as described below.

Initial Medium: The bonito hydrolysate prepared in Reference Example 1 was added to a mammal-derived component free medium at 15 g/L. After dissolution, the resultant medium was filter-sterilized.

Feed Medium: The concentrations of the components in the mammal-derived component free medium used as the initial medium were made about 4-fold relative to the initial medium. The bonito hydrolysate (75 g/L) was added to the resultant medium and dissolved, followed by filter sterilization.

Cell: Humanized PM-1 antibody (anti-human IL-6 receptor antibody)-producing CHO cell strain prepared using the human elongation factor Iα promoter disclosed in Example 10 of International Publication WO 92/19759 based on the method disclosed in Reference Example 2 of Japanese Unexamined Patent Publication No. H8-99902. The class of this antibody is IgG1.

Figure 2:
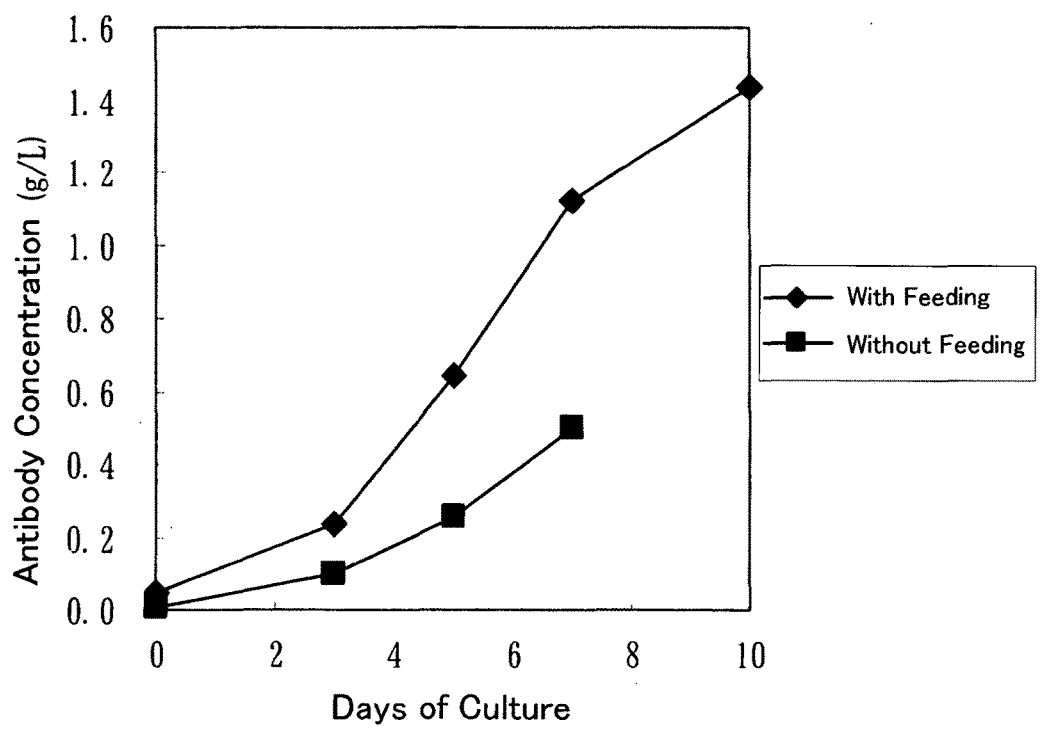
FIG. 2 is a graph showing the concentrations (g/L) of an antibody produced in culture media by CHO cells which were cultured in a mammal-derived component free medium supplemented with 15 g/L of bonito hydrolysate (initial medium) and a mammal-derived component free medium supplemented with 75 g/L of bonito hydrolysate (feed medium).

The initial medium was added to a jar-type culture device. The above-described CHO cell strain was added thereto at $1 \times 10^6$ cells/mL when the feed medium was to be fed and at $0.5 \times 10^6$ cells/mL when the feed medium was not to be fed. Then, culturing was started at 37° C. under 10% $CO_2$. In fed-batch culture, the feed medium was fed at a constant flow rate from day 2 of culture, and cells were cultured until day 10. Sampling was performed at the start of culture and at days 3, 5, 7 and 10. The culture supernatant of each sample was subjected to affinity chromatography using a protein A column to determine the concentration of antibody produced. As shown in FIG. 2, the antibody concentration was about 0.5 g/L after 7 days culture when the feed medium was not fed. On the other hand, when the solution containing the bonito hydrolysate was fed, high antibody concentrations could be achieved (1.1 g/L or more after 7 days culture and exceeding 1.4 g/L after 10 days culture).

Example 3

Fed-Batch Culture Using a Bonito Hydrolysate

The compositions of the media and the method of preparation thereof are as described below.

Initial Medium: The bonito hydrolysate prepared in Reference Example 1 was added to a mammal-derived component free medium at 5 g/L. After dissolution, the resultant medium was filter-sterilized. As a control, the same medium without the bonito hydrolysate was used.

Feed Medium: The concentrations of the components in the mammal-derived component free medium used as the initial medium were made 2-fold relative to the initial medium. The bonito hydrolysate (30 g/L) was added to the resultant medium and dissolved, followed by filter sterilization. As a control, the same medium without the bonito hydrolysate was used.

Cell: MPL-binding single chain $(Fv)_2$ $(sc(Fv)_2)$-producing, recombinant CHO cell prepared by the method disclosed in International Publication WO 2005/056604.

Figure 3:
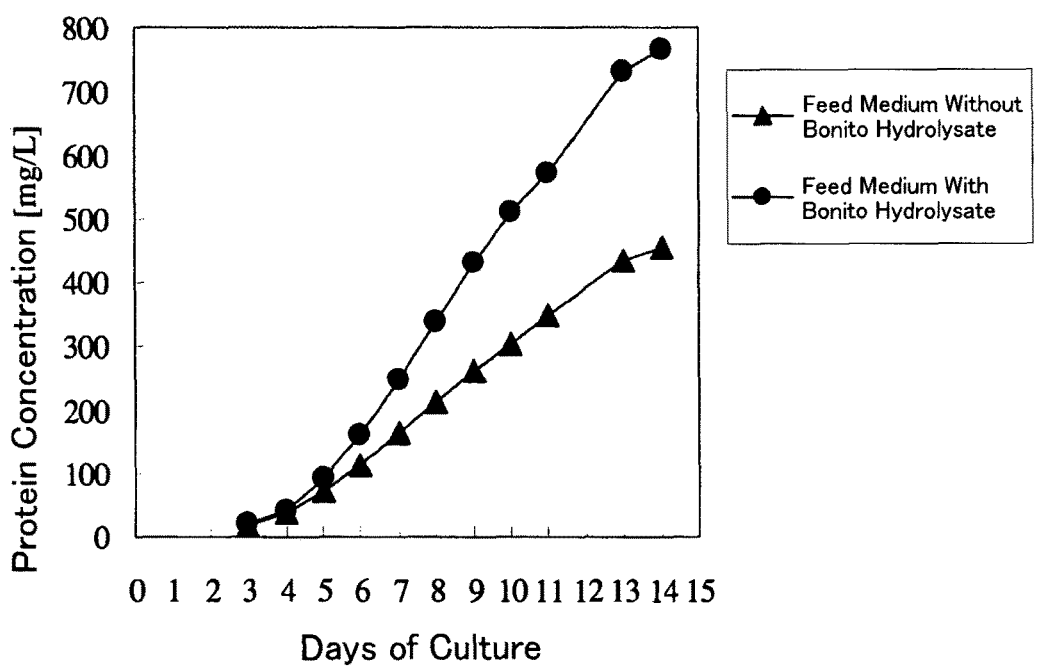
FIG. 3 is a graph showing the concentrations (g/L) of an protein produced in culture media by CHO cells which were cultured in a mammal-derived component free medium supplemented with 5 g/L of bonito hydrolysate (initial medium) and a mammal-derived component free medium supplemented with 30 g/L of bonito hydrolysate (feed medium).

Culture Results:

The initial medium was added to a jar-type culture device. The above-described CHO cell strain was added thereto at $3 \times 10^5$ cells/mL. Then, culturing was started at 37° C. under 10% $CO_2$. The feed medium was fed at a constant flow rate from day 3 of culture, and cells were cultured until day 14. Sampling was performed from time to time during culturing. For the culture supernatant of each sample, the concentration of protein was determined by BIACORE method using the part of MPL amino acid sequence to which $sc(Fv)_2$ binds. As shown in FIG. 3, the protein concentration after 14 days culture was about 450 mg/L when the feed medium without the bonito hydrolysate was fed. On the other hand, when the solution with the bonito hydrolysate was fed, a high protein concentration (exceeding 760 mg/L after 14 days culture) could be achieved.

Reference Example 1

Preparation of an Enzymatic Degradation Product of Bonito

A commercially available bonito was used as fish meat. To 840 kg of minced bonito, 1,200 kg of water was added. The mixture was incubated for 1 hour together with 3.2 kg of plant-derived papain at pH 6.0 and at 65° C. for enzymatic degradation. Then, enzymatic degradation was further carried out with 3.2 kg of mold-derived exopeptidase for 15 hours under the above conditions, whereafter the system was heated at 95° C. to inactivate the enzymes. Then, the system was centrifuged and filtered to remove insolubles and oils. The residue was concentrated to obtain about 150 kg of an enzymatic degradation product of fish meat (bonito).

All publications, patents and patent applications cited herein are incorporated herein by reference in their entirety.

INDUSTRIAL APPLICABILITY

According to the present invention, it is possible to culture a cell stably without using expensive proteins, such as fetal bovine serum, which vary greatly in quality. Furthermore, by culturing a cell according to the method of the present invention, risks of contamination with abnormal prions or viruses which have become serious problems recently can be eliminated, and safe biopharmaceuticals can be produced and supplied in large quantities.

The invention claimed is:

1. A method of producing an antibody by culturing a CHO cell, comprising starting culturing in an initial medium comprising 5-15 g/L of an enzymatic degradation product of fish meat added thereto and feeding at least once a feed medium comprising 30-75 g/L of an enzymatic degradation product of fish meat to the medium during culturing, wherein:
    (i) the cell is cultured by fed-batch culture,
    (ii) the volume ratio of feed medium: initial medium is 0.2:1 to 0.3:1,
    (iii) the cell is cultured for about 7 to about 14 days, and
    (iv) the cell is a cell into which a gene encoding the antibody has been transferred.

2. The method according to claim 1, wherein the antibody is an IgG antibody.

3. The method according to claim 1, wherein the cell is cultured for 7-10 days.

4. The method according to claim 1, wherein the initial and feed media do not contain any mammal-derived component isolated from mammals.

5. The method according to claim 1, wherein the antibody is selected from the group consisting of anti-ganglioside GM3 human antibody, anti-human IL-6 receptor antibody, and MPL-binding single chain $(Fv)_2$.

* * * * *